US011578300B2

(12) United States Patent
Uematsu et al.

(10) Patent No.: US 11,578,300 B2
(45) Date of Patent: Feb. 14, 2023

(54) TEST APPARATUS

(71) Applicant: Hitachi High-Tech Corporation, Tokyo (JP)

(72) Inventors: Chihiro Uematsu, Tokyo (JP); Muneo Maeshima, Tokyo (JP); Akira Masuya, Tokyo (JP)

(73) Assignee: Hitachi High-Tech Corporation, Tokyo (JP)

( * ) Notice: Subject to any disclaimer, the term of this patent is extended or adjusted under 35 U.S.C. 154(b) by 295 days.

(21) Appl. No.: 17/121,712

(22) Filed: Dec. 14, 2020

(65) Prior Publication Data

US 2021/0189321 A1 Jun. 24, 2021

Related U.S. Application Data

(62) Division of application No. 15/125,980, filed as application No. PCT/JP2014/074961 on Sep. 19, 2014, now Pat. No. 10,900,011.

(30) Foreign Application Priority Data

Mar. 19, 2014 (JP) ................................. 2014-057138

(51) Int. Cl.
 *C12M 1/34* (2006.01)
 *C12M 1/32* (2006.01)
 *C12Q 1/04* (2006.01)

(52) U.S. Cl.
 CPC ............ *C12M 41/46* (2013.01); *C12M 23/12* (2013.01); *C12M 41/12* (2013.01); *C12M 41/36* (2013.01); *C12Q 1/04* (2013.01)

(58) Field of Classification Search
 CPC .............................. C12M 41/36; C12M 41/46
 See application file for complete search history.

(56) References Cited

U.S. PATENT DOCUMENTS 4,448,534 A 5/1984 Wertz et al.
5,501,959 A 3/1996 Lancaster et al.
(Continued)

FOREIGN PATENT DOCUMENTS

CN 1289365 A 3/2001
CN 1333374 A 1/2002
(Continued)

OTHER PUBLICATIONS

Extended European Search Report issued in European Application No. 21190236.6 dated Jan. 4, 2022 (eight (8) pages).
(Continued)

*Primary Examiner* — Jonathan M Hurst
(74) *Attorney, Agent, or Firm* — Crowell & Moring LLP

(57) ABSTRACT

Provided is a test apparatus in which a test for bacterial identification or antimicrobial susceptibility can be promptly determined. A division state of bacteria is monitored by performing microscopic observation of shapes and the number of the bacteria in each of wells in a culture plate for bacterial identification culture or an antimicrobial susceptibility test, and it is determined whether or not the bacteria grow in a stage shifted from an induction phase to a logarithmic phase, with reference to an image obtained through microscopic observation. In addition, determination performed based on turbidity in the related art may be combined with determination performed based on microscopic observation in which change and the like in the shapes of the bacteria are monitored. Accordingly, it is possible to realize a highly accurate test result.

7 Claims, 15 Drawing Sheets

(56) References Cited

U.S. PATENT DOCUMENTS

| | | | |
|---|---|---|---|
| 5,660,998 | A | 8/1997 | Naumann |
| 6,096,272 | A | 8/2000 | Clark et al. |
| 6,792,132 | B1 | 9/2004 | Hara et al. |
| 6,872,545 | B2 | 3/2005 | Griner |
| 2002/0064867 | A1 | 5/2002 | Clark et al. |
| 2003/0082516 | A1 | 5/2003 | Straus |
| 2006/0210962 | A1 | 9/2006 | Imaizumi et al. |
| 2008/0317815 | A1 | 12/2008 | Davies |
| 2010/0112623 | A1 | 5/2010 | Fujimoto |
| 2012/0034596 | A1 | 2/2012 | Seidl et al. |
| 2012/0088263 | A1 | 4/2012 | Bruno |
| 2012/0258525 | A1 | 10/2012 | Iizumi et al. |
| 2013/0324437 | A1 | 12/2013 | Pogliano et al. |

FOREIGN PATENT DOCUMENTS

| | | | |
|---|---|---|---|
| CN | 1367259 | A | 9/2002 |
| CN | 1582327 | A | 2/2005 |
| CN | 101130808 | A | 2/2008 |
| CN | 101787346 | A | 7/2010 |
| CN | 102471750 | A | 5/2012 |
| JP | 63-188383 | A | 8/1988 |
| JP | 4-346779 | A | 12/1992 |
| JP | 5-84098 | A | 4/1993 |
| JP | 2001-112498 | A | 4/2001 |
| JP | 2005-502354 | A | 1/2005 |
| JP | 2005-261260 | A | 9/2005 |
| JP | 2008-86279 | A | 4/2008 |
| JP | 2010-44085 | A | 2/2010 |
| JP | 2011-250808 | A | 12/2011 |
| JP | 2012-524527 | A | 10/2012 |
| JP | 2013-176332 | A | 9/2013 |
| JP | 2013-538567 | A | 10/2013 |
| JP | 2013-255445 | A | 12/2013 |
| WO | WO 02/094976 | A2 | 11/2002 |
| WO | WO 03/022999 | A2 | 3/2003 |
| WO | WO 2010/020863 | A2 | 2/2010 |

OTHER PUBLICATIONS

International Search Report (PCT/ISA/210) issued in PCT Application No. PCT/JP2014/074961 dated Dec. 22, 2014 with English translation (Five (5) pages).

Japanese-language Written Opinion (PCT/ISA/237) issued in PCT Application No. PCT/JP2014/074961 dated Dec. 22, 2014 (Five (5) pages).

Chinese Office Action issued in counterpart Chinese Application No. 201480077083.2 dated Jun. 20, 2017 (eight (8) pages).

Extended European Search Report issued in counterpart European Patent Application No. 14886521.5 dated Nov. 14, 2017 (Eight (8) pages).

Japanese-language Office Action issued in counterpart Japanese Application No. 2014-057138 dated Nov. 28, 2017 (Four (4) pages).

Japanese-language Office Action issued in counterpart Japanese Application No. 2014-057138 dated Jun. 12, 2018 (four pages).

Shibata et al., "Assay of MIC for *Candida* by modified endpoint determination", Aug. 2003, pp. 470-476, vol. 51, No. 8, with English abstract.

Japanese-language Office Action issued in counterpart Japanese Application No. 2014-057138 dated Jul. 23, 2019 (six (6) pages).

Japanese-language Office Action issued in counterpart Japanese Application No. 2018-169292 dated Sep. 3, 2019 (seven (7) pages).

[Fig. 1]
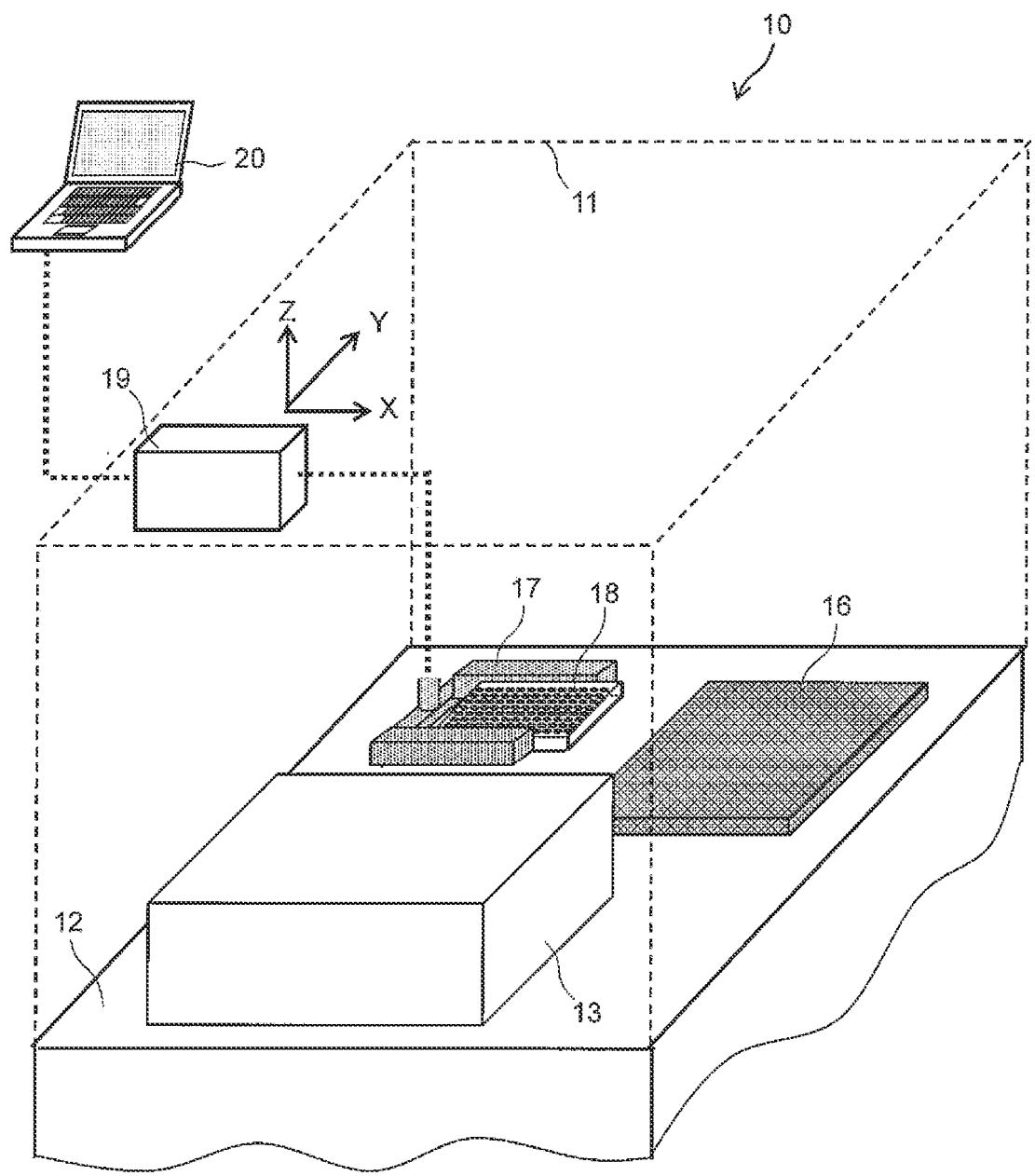

[Fig. 2]
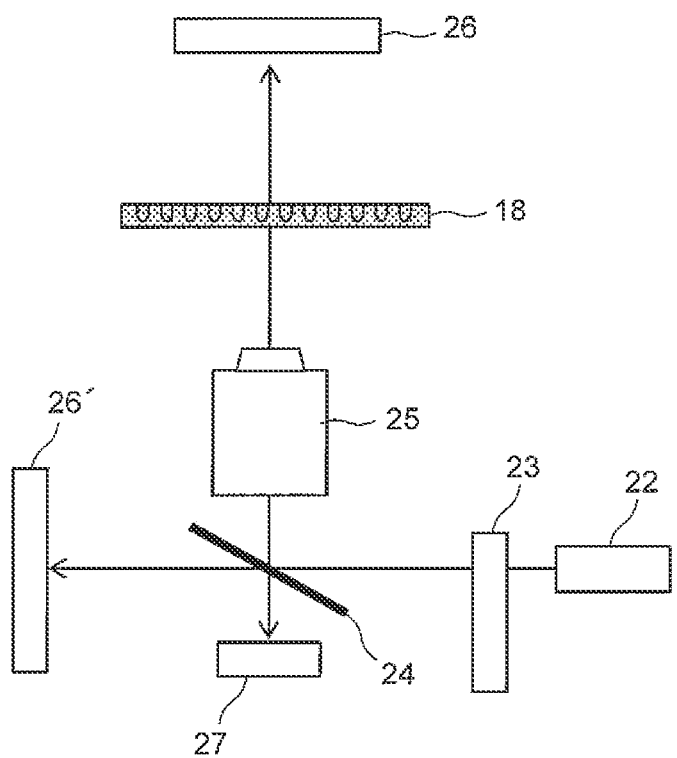

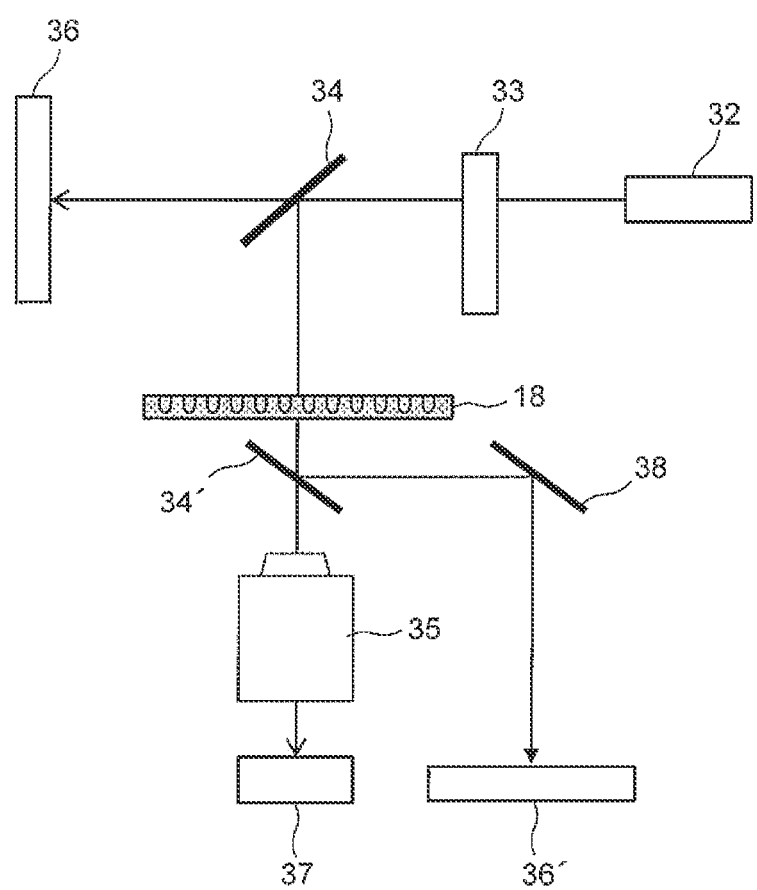
[Fig. 3]

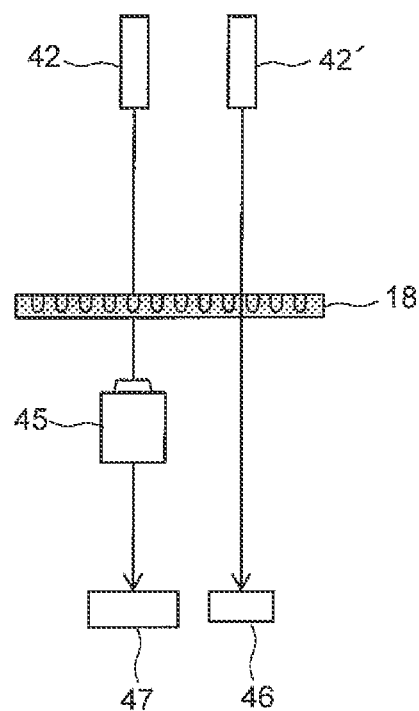
[Fig. 4]

[Fig. 5]
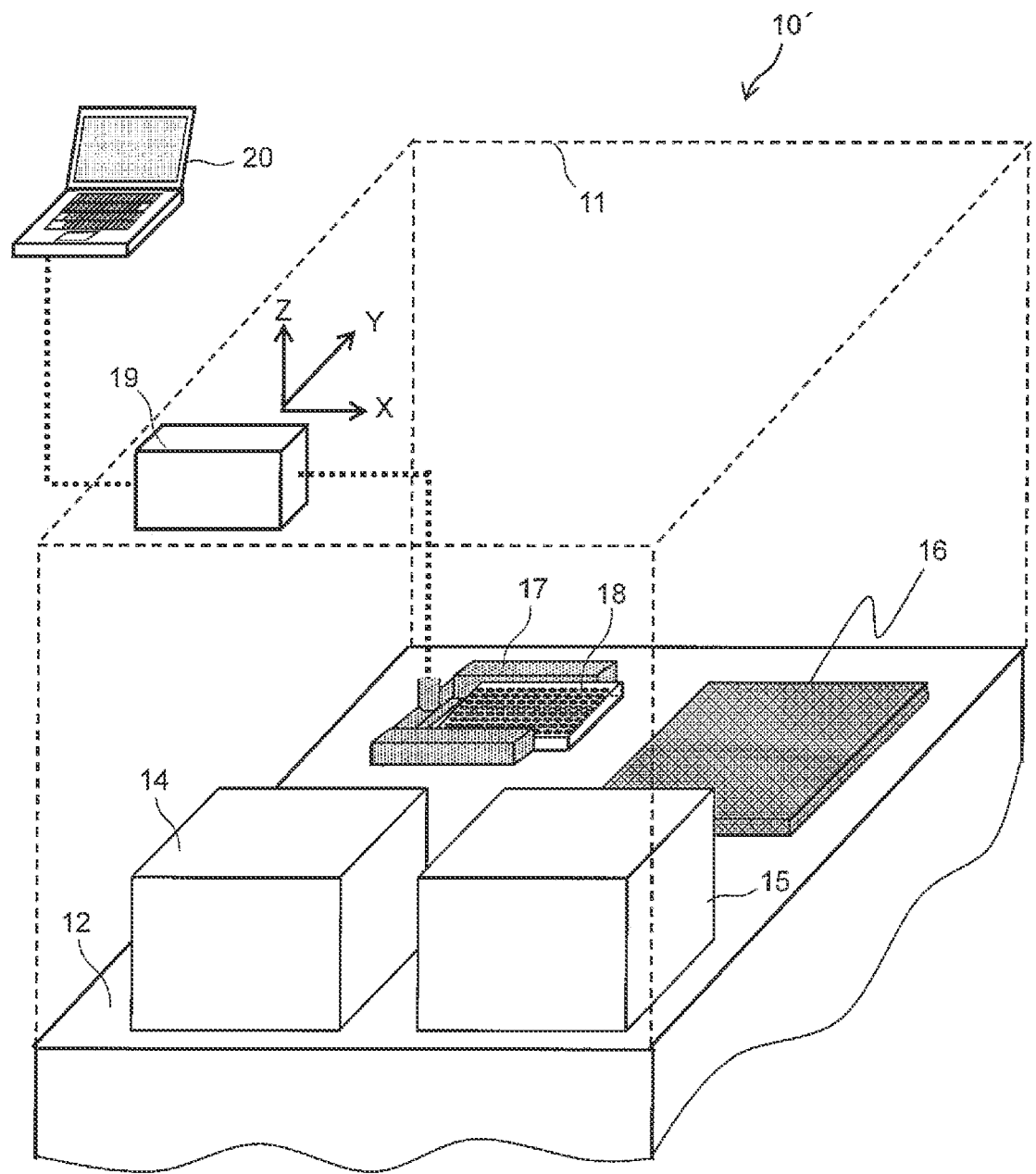

[Fig. 6]
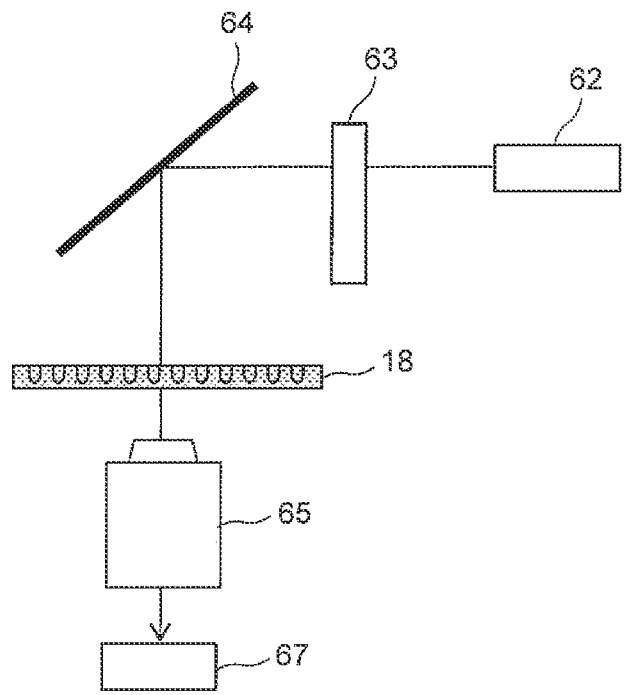
[Fig. 7]
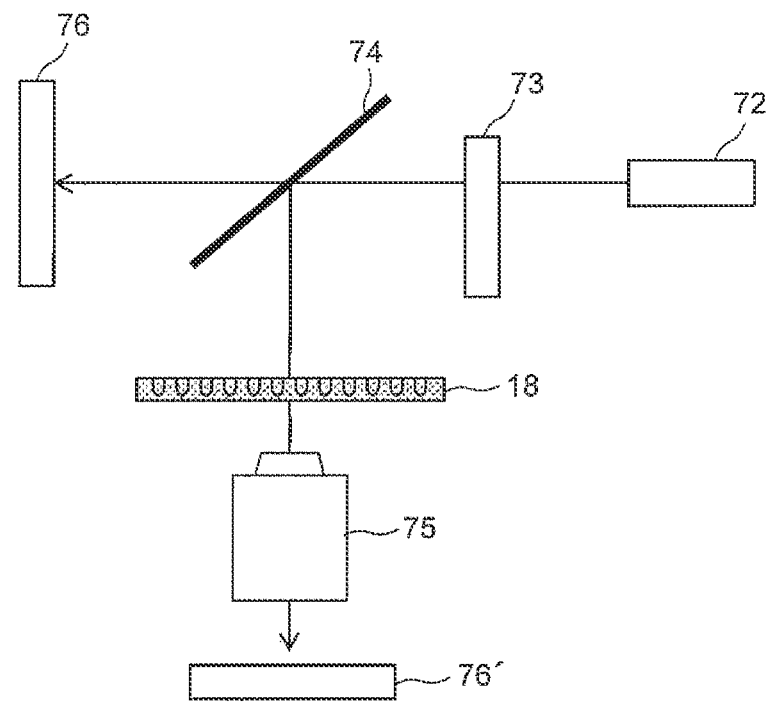

[Fig. 8]
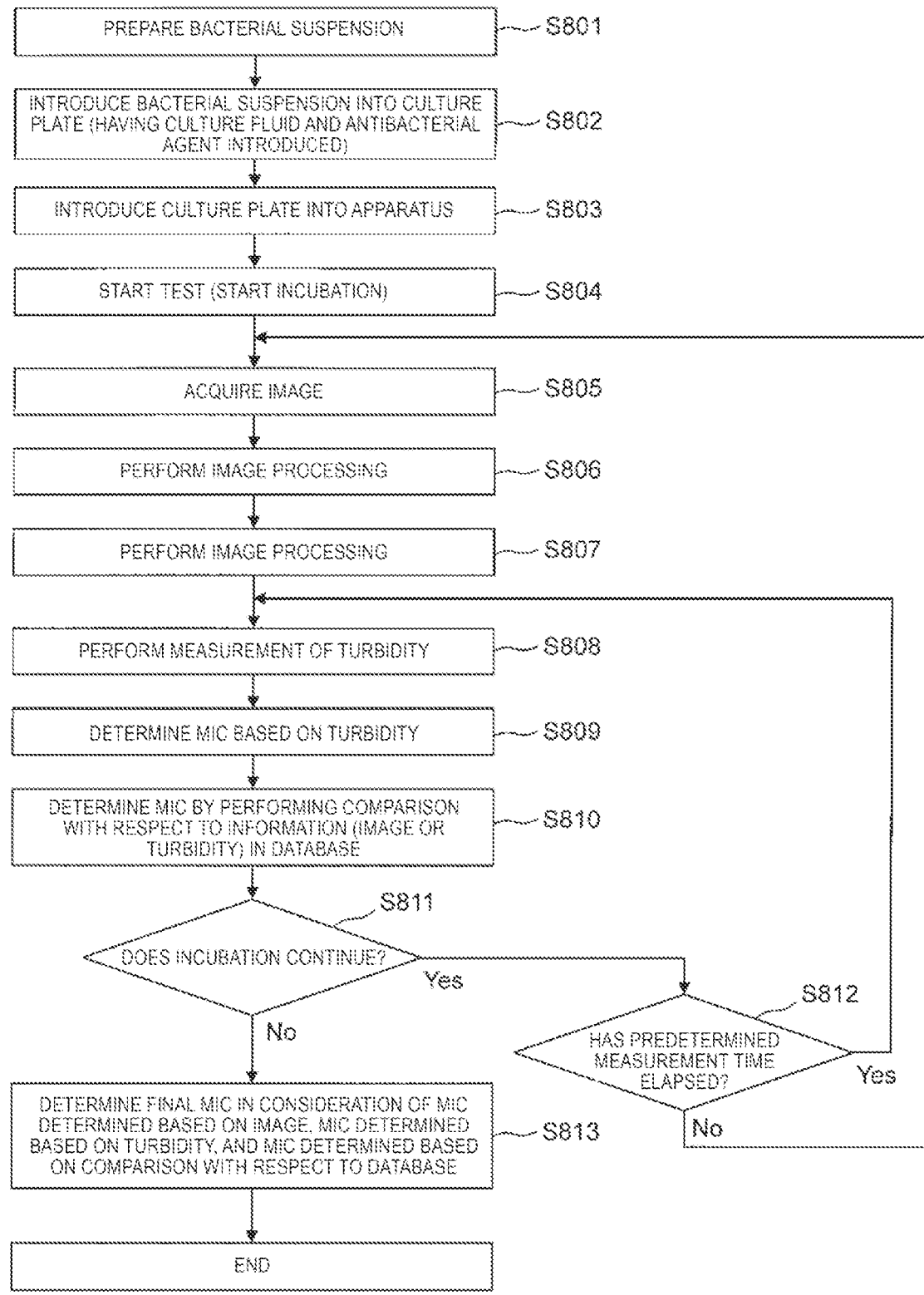

[Fig. 9]
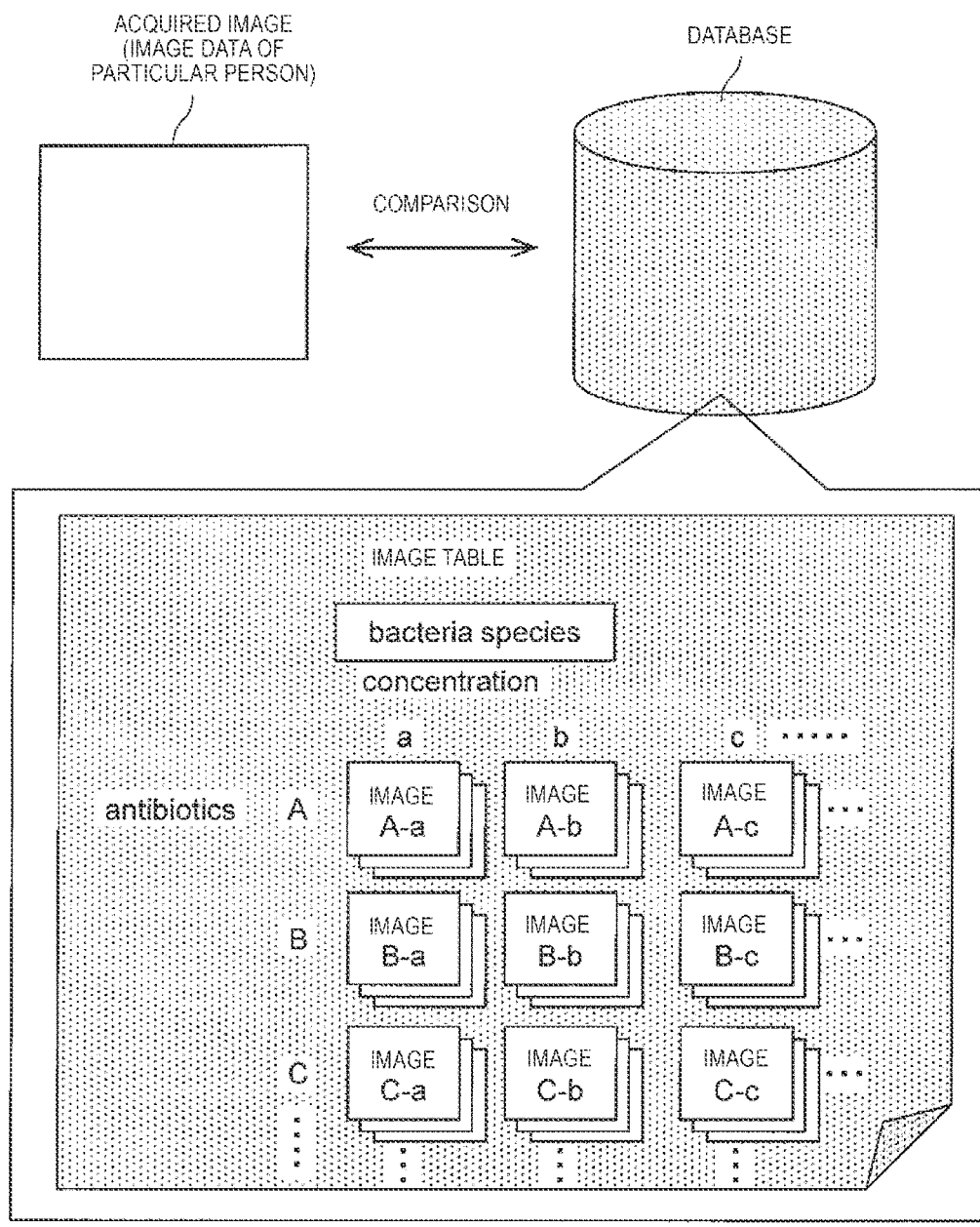

FIG. 10A  FIG. 10B  FIG. 10C  FIG. 10D
0 μg/mL
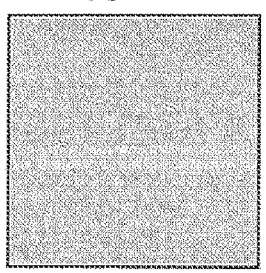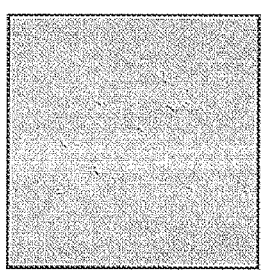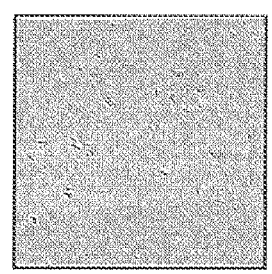
0 min  90 min  150 min  210 min
─── 50 μm
FIG. 11A  FIG. 11B  FIG. 11C  FIG. 11D
0.5 μg/mL
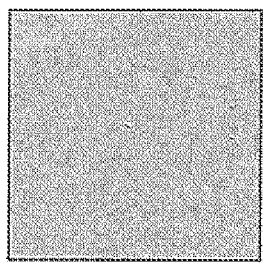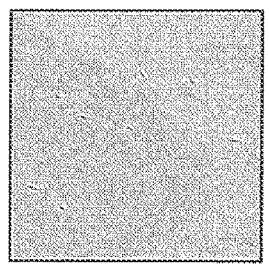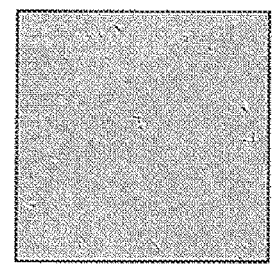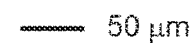
0 min  90 min  150 min  210 min
─── 50 μm
FIG. 12A  FIG. 12B  FIG. 12C  FIG. 12D
1.0 μg/mL
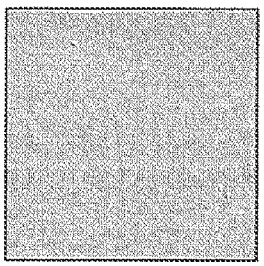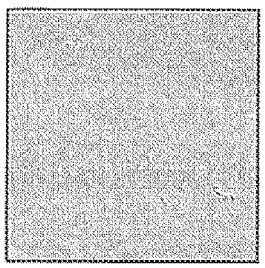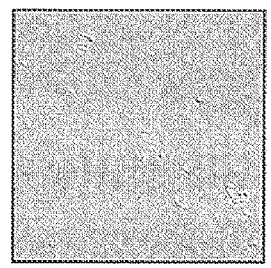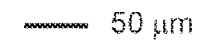
0 min  90 min  150 min  210 min
─── 50 μm

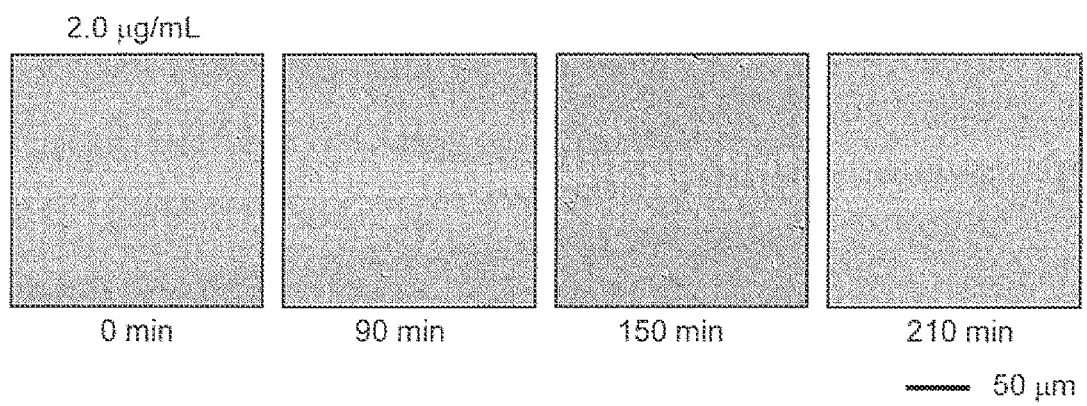
FIG. 13A   FIG. 13B   FIG. 13C   FIG. 13D
2.0 μg/mL
0 min   90 min   150 min   210 min
—— 50 μm
[Fig. 14]
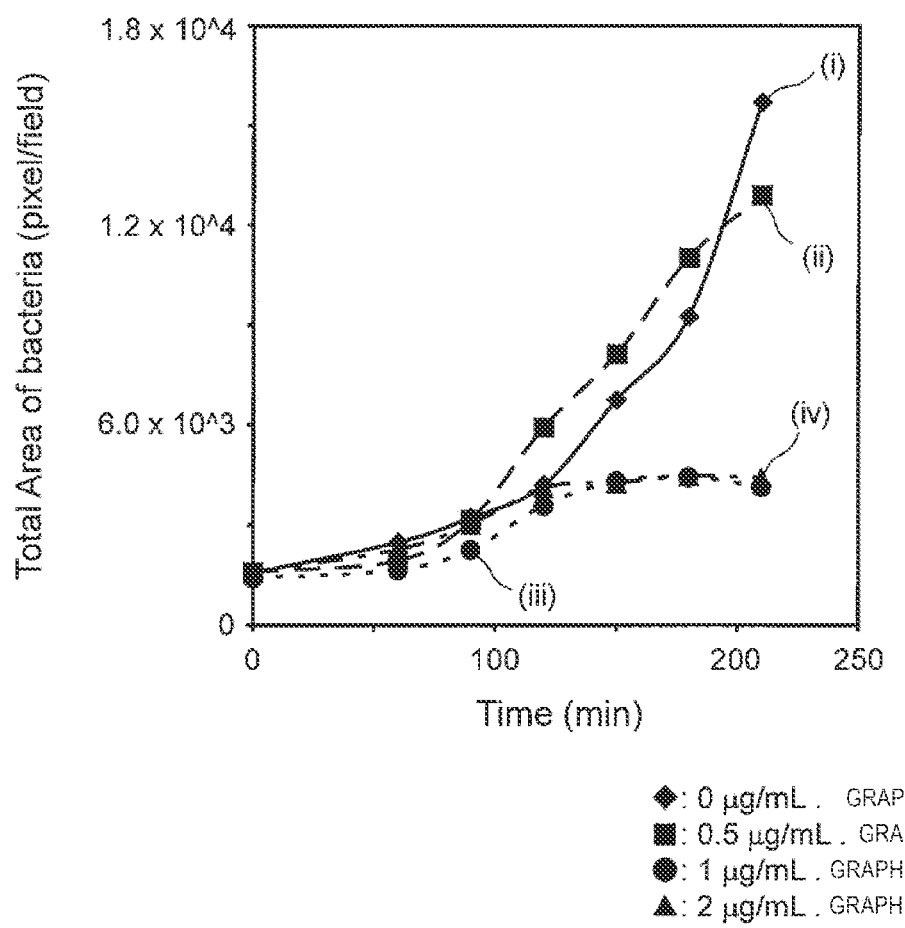
◆: 0 μg/mL . GRAPH (i)
■: 0.5 μg/mL . GRAPH (ii)
●: 1 μg/mL . GRAPH (iii)
▲: 2 μg/mL . GRAPH (iv)

[Fig. 19]
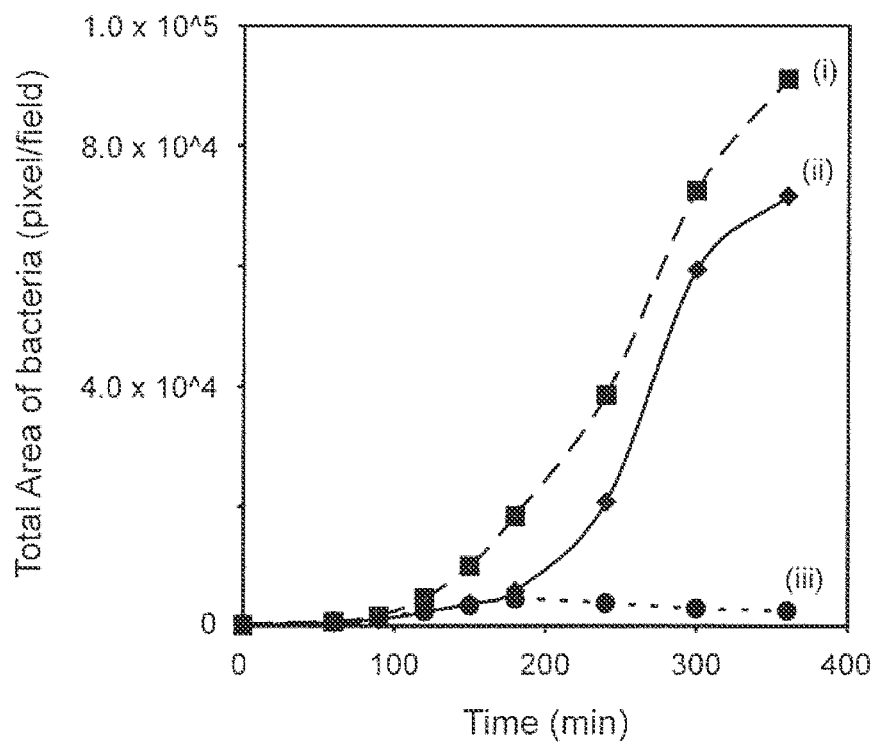
◆: 0 μg/mL : GRAPH (i)
■: 2 μg/mL : GRAPH (ii)
●: 16 μg/mL : GRAPH (iii)
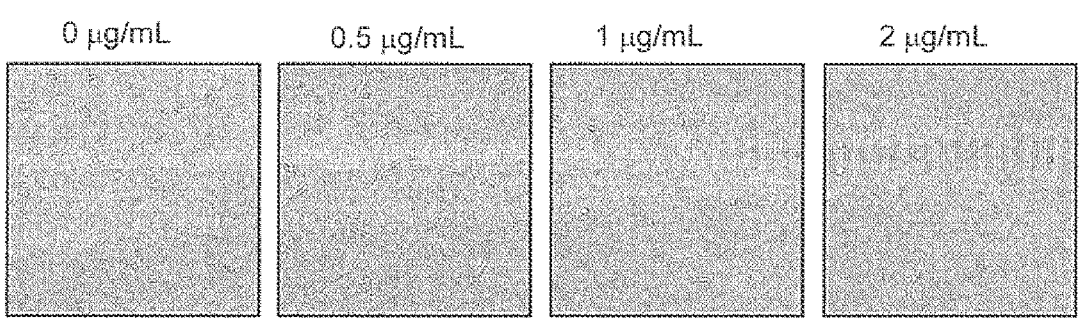
FIG. 20A     FIG. 20B     FIG. 20C     FIG. 20D
0 μg/mL     0.5 μg/mL     1 μg/mL     2 μg/mL 0 µg/mL 0.5 µg/mL 1 µg/mL 2 µg/mL

TEST APPARATUS

CROSS-REFERENCE TO RELATED APPLICATIONS

This application is a Divisional of U.S. application Ser. No. 15/125,980, filed Sep. 14, 2016, which is a 371 of international PCT Application No. PCT/JP2014/074961, filed Sep. 19, 2014, and is based on and claims priority from Japanese Patent Application No. 2014-057138, filed Mar. 19, 2014, the disclosures of which are expressly incorporated by reference herein.

TECHNICAL FIELD

The present invention relates to a test apparatus, and for example, relates to a test apparatus used in an identification test and an antimicrobial susceptibility test of bacteria or fungi.

BACKGROUND ART

Recently, antibiotics have been overused with respect to infectious disease patients, resulting in an increase of the proportion of drug-resistant bacteria. Accordingly, the number of instances of hospital acquired infection tends to increase as well. However, the development of new antibiotics has decreased due to slimmer profit margins, and the number of types of the antibiotics approved by US FDA has been decreasing every year. Therefore, when an infectious disease occurs, it is vitally important to achieve early recovery of patients, to prevent the spread of hospital acquired infection, and to suppress the emergence of drug-resistant bacteria by carrying out an identification test and an antimicrobial susceptibility test of the bacterial species of the causative bacteria thereof and using antibiotics properly.

In a test method which is generally carried out in bacteriological test laboratories, a causative bacterium of an infectious disease is cultured and identification and antimicrobial susceptibility of the bacterial species are determined based on the presence or absence of growth thereof. First, a specimen such as blood, a throat swab, and sputum is collected from a patient. Then, isolation culture for obtaining the infection causative bacterium in a single colony is performed for twenty-four hours. A bacterial suspension is prepared from the single colony, and culture for examining identification culture or antimicrobial susceptibility is performed for twenty-four hours. The determination result of the antimicrobial susceptibility test is obtained and appropriate medication is performed after three days, for example, after the specimen is collected from the patient. An infection causative bacterium which has a slow growth rate and needs to be cultured for a long time requires more days.

For example, as a test apparatus for achieving automation and energy-saving in isolation culture, a test apparatus which acquires an image of bacterial colonies in a culture dish and measures micro-organisms or cells, and the like have been developed (refer to PTL 1).

CITATION LIST

Patent Literature

PTL 1: JP-A-2005-261260

SUMMARY OF INVENTION

Technical Problem

However, in a case of using an apparatus disclosed in PTL 1, since a bacterium needs to grow until the bacteria become determinable, there is a problem in that it takes time to make determination. For example, in a case of bacteria such as *Pseudomonas aeruginosa* which slowly grows, the bacteria needs to be cultured for at least eight hours or longer after a single colony is obtained. In addition, in order to perform a bacterial identification test or an antimicrobial susceptibility test, it is necessary to prepare a bacterial suspension from a single colony which is obtained after isolation culture and to perform culture for examining identification culture or antimicrobial susceptibility for twenty-four hours. As a result of being cultured, bacteria are divided under the conditions where bacteria grow, and turbidity of a culture liquid increases. Since it is determined whether or not the bacteria growth based on whether or not turbidity increases, every shape of the bacteria cannot be utilized for determination.

The present invention has been made in consideration of the above-referenced circumstances, and there is provided a technique in which determination of bacterial identification or antimicrobial susceptibility can be promptly performed.

Solution to Problem

In order to solve the aforementioned problem, in the present invention, there is provided a configuration for determining whether or not bacteria growth, by performing microscopic observation of a culture liquid for bacterial identification culture or antimicrobial susceptibility test.

More specifically, according to the present invention, there is provided a test apparatus which performs an identification test or an antimicrobial susceptibility test of bacteria or fungi. The test apparatus includes a temperature control unit that controls a temperature of a culture plate having a plurality of wells and retaining a culture liquid which contains the bacteria or the fungi in each well; a microscopic observation optical system; and a transportation mechanism that transports the culture plate between the temperature control unit and the microscopic observation optical system. The microscopic observation optical system is used to perform microscopic observation of the bacteria or the fungi in the culture liquid included in each of the wells in the culture plate.

Other features related to the present invention will be clarified by the contents of this Description and the accompanying drawings. In addition, aspects of the present invention will be achieved and realized in forms of the elements, combinations of various elements, the detailed description below, and the accompanying Claims.

The contents in this Description are merely typical examples, and it is necessary to understand that Claims and application examples of the present invention are not limited by any means.

Advantageous Effects of Invention

According to the present invention, determination of bacterial identification or antimicrobial susceptibility can be promptly performed.

BRIEF DESCRIPTION OF DRAWINGS

FIG. 1 is a schematic diagram illustrating a configuration example of a bacteriological test apparatus, according to an embodiment of the present invention.

FIG. 2 is a schematic diagram illustrating a configuration example of an optical system of the bacteriological test apparatus, according to the embodiment of the present invention.

FIG. 3 is a schematic diagram illustrating another configuration example of the optical system of the bacteriological test apparatus, according to the embodiment of the present invention.

FIG. 4 is a schematic diagram illustrating further another configuration example of the optical system of the bacteriological test apparatus, according to the embodiment of the present invention.

FIG. 5 is a schematic diagram illustrating another configuration example of the bacteriological test apparatus, according to the embodiment of the present invention.

FIG. 6 is a schematic diagram illustrating a configuration example of a microscopic observation optical system applied to another configuration example of the bacteriological test apparatus, according to the embodiment of the present invention.

FIG. 7 is a schematic diagram illustrating another configuration example of the microscopic observation optical system applied to another configuration example of the bacteriological test apparatus, according to the embodiment of the present invention.

FIG. 8 is a flow chart for describing MIC determination processing carried out by the bacteriological test apparatus, according to the embodiment of the present invention.

FIG. 9 is a diagram illustrating a concept of image comparison performed by the bacteriological test apparatus, according to the embodiment of the present invention.

FIGS. 10A-10D are images of Example 1 obtained through a susceptibility test (Exemplary Embodiment 1) performed by the bacteriological test apparatus.

FIGS. 11A-11D are images of Example 2 obtained through the susceptibility test (Exemplary Embodiment 1) performed by the bacteriological test apparatus.

FIGS. 12A-12D are images of Example 3 obtained through the susceptibility test (Exemplary Embodiment 1) performed by the bacteriological test apparatus.

FIGS. 13A-13D are images of Example 4 obtained through the susceptibility test (Exemplary Embodiment 1) performed by the bacteriological test apparatus.

FIG. 14 is a graph illustrating a state of growth of bacteria obtained through the susceptibility test (Exemplary Embodiment 1) performed by the bacteriological test apparatus.

FIG. 19 is a graph illustrating a state of growth of bacteria obtained through the susceptibility test (Exemplary Embodiment 2) performed by the bacteriological test apparatus.

FIGS. 20A-20D are images of Example 1 obtained through a susceptibility test (Exemplary Embodiment 3) performed by the bacteriological test apparatus.

DESCRIPTION OF EMBODIMENT

Figure 15A:
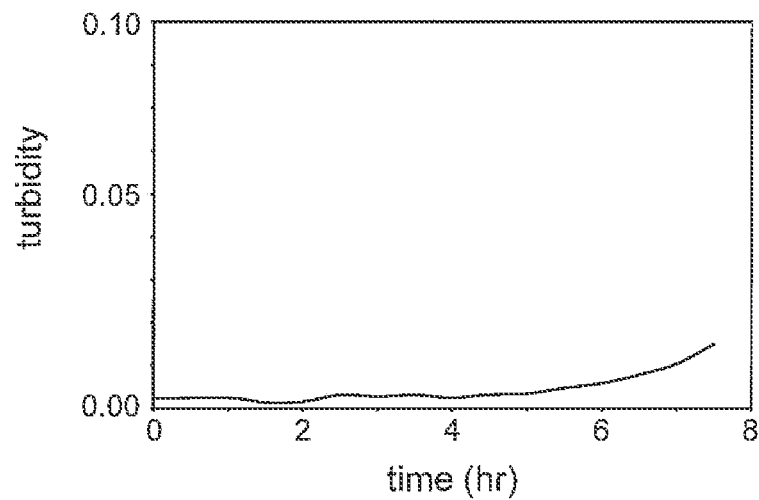
FIGS. 15A and 15B are other graphs illustrating the state of growth of the bacteria obtained through the susceptibility test (Exemplary Embodiment 1) performed by the bacteriological test apparatus.

Hereinafter, with reference to the accompanying drawings, an embodiment of the present invention will be described. In the accompanying drawings, there are cases where the same number is applied to the elements having the same function. The accompanying drawings specifically illustrate an embodiment and implementation examples based on the principle of the present invention. However, the accompanying drawings are provided so as to help others in understanding the present invention and will never be used in order to limitedly interpret the present invention.

The present embodiment is described in sufficient detail for those skilled in the art to carry out the present invention. However, other types of implementation and forms can be applied. It is necessary to understand that changes in the configuration and the structure can be made and the elements can be variously replaced without departing from the scope and the gist of the technical idea of the present invention. Thus, the following description shall not be interpreted in a manner of being limited thereto.

Following is the description of the embodiment and exemplary embodiments having bacteria as a test target. However, without being limited thereto, fungi may be adopted as the test target.

<Configuration of Test Apparatus>

FIG. 1 is a diagram illustrating a schematic configuration of a bacteriological test apparatus (hereinafter, there are cases of being referred to as "a bacterial test apparatus" or "a test apparatus") 10, according to the embodiment of the present invention. The bacteriological test apparatus 10 includes a cover 11, a placement table 12, a microscopic observation optical system and a turbidity measurement optical system 13, a temperature controller 16, a gripper 17 for transporting a culture plate (microplate) 18, and a drive control device 19 which controls movement and positioning of the gripper 17. In addition, the bacteriological test apparatus 10 includes a computer (the processor) 20 for inputting information related to processing conditions and biological samples, information related to types and concentrations of antibacterial agents, information related to patient specimens, and other various types of information.

A test performed by using the bacteriological test apparatus 10 is an identification test or an antimicrobial susceptibility test of bacteria or fungi. Here, the identification test denotes a test in which bacteria or fungi are cultured in culture liquids respectively having solution compositions different from each other and the bacteria or the fungi are identified based on conditions of growth. In addition, the antimicrobial susceptibility test denotes a test in which bacteria or fungi are cultured in culture liquids respectively containing various types of antimicrobials having predetermined concentrations and conditions of growth of the bacteria or the fungi are examined for drug resistance, or a test determining the minimum inhibitory concentration (MIC) of bacteria or fungi (MIC determination).

Target bacteria to be examined by using the test apparatus of the present invention are not particularly limited. *Staphy-*

*lococcus aureus, Enterococcus faecalis, Streptococcus pneumoniae, E coli, Pseudomonas aeruginosa, Klebsiella pneumoniae*, and the like can be exemplified.

When a test is performed by using the test apparatus of the present invention, in many cases, a bacterial suspension is prepared by using a single colony obtained from a clinical specimen through isolation culture. However, in a case where the possibility of contamination with respect to the clinical specimen is low and a single species of bacterium is included, without preparing the bacterial suspension, the specimen may be used with no change or may be used by being appropriately diluted.

When a test is performed by using the test apparatus of the present invention, it is desirable that specimens are collected, are carried, and are subjected to isolation culture in accordance with a method recommended by the Clinical and Laboratory Standards Institute (CLSI, Wayne, Pa.). Preparation of antibacterial drugs and preparation of culture mediums are performed in a similar manner. However, the preparations are not limited thereto. In addition, it is also desirable that a culture temperature and a culture liquid to be used are adopted in a similar manner based on the method recommended by CLSI. However, the culture temperature and the culture liquid are not limited thereto.

When a test is performed by using the test apparatus of the embodiment of the present invention, culture is performed by mixing a bacterial suspension prepared from a specimen with a culture liquid in the culture plate 18. In a case where the identification test is performed, the culture liquids in wells in the culture plate 18 respectively have the compositions different from each other. In addition, in a case where the antimicrobial susceptibility test is performed, antibacterial agents different from each other are set so as to be respectively contained in the culture liquids in the wells in particular concentrations. The identification test and the antimicrobial susceptibility test may be simultaneously performed by inputting culture liquids for identification tests having compositions different from each other to a portion of the wells in the culture plate 18, and by using the culture plate in which antibacterial agents for antimicrobial susceptibility tests different from each other are set to be contained in another portion of the wells in particular concentrations.

After the bacterial suspension is introduced into the culture plate 18, the bacterial suspension is in a state of being mixed with the culture liquid which is included in each of the wells, and the temperature controller 16 is set to a temperature of approximately 35° C. Culture is performed by performing incubation such that the temperature of each of the wells in the culture plate 18 is in the vicinity of the set temperature. Then, while performing the incubation, the bacteria included in each of the wells are monitored through the microscopic observation optical system. The microscopic observation (monitoring) may be performed for a set period of time from the start of the incubation till the end thereof by continuously monitoring the state of bacterial growth. Otherwise, a suitable time may be set and monitoring is performed every set time thereof so as to be able to be compared with the monitored result at the time of starting the incubation. In addition, similar to the bacteriological test apparatus in the related art, the turbidity of each of the wells may be measured through the turbidity measurement optical system while incubating the culture plate 18. The measured result may be compared with the monitored result of the microscopic observation optical system.

The image obtained as a result of the microscopic observation and the data obtained as a result of the measurement of the turbidity are stored and preserved in a control PC, thereby being utilized for bacterial identification, the MIC determination, and the like. The image obtained through the test is compared with a database (DB) including images and turbidity data obtained thus far through the test, and the MIC determination is performed. In addition, a newly obtained image may be added to the DB of the control PC together with information for the bacterial species, the concentrations of the antibacterial agents, and the like. Moreover, the MIC determined based on the image obtained through the microscopic observation and the MIC determined based on the data of the measurement of the turbidity can be synthetically determined so that the final MIC can be calculated. In other words, in a case where the MIC determination is performed once through the microscopic observation (in a case where the bacterial growth is suppressed or the bacteria become extinct with success after the elapse of a predetermined time which is shorter than the time for normal measurement of the turbidity), the measurement of the turbidity may be performed in order to confirm whether or not the final MIC can be obtained. In addition, in this case, in a case where it is confirmed that the bacterial growth cannot be suppressed through the microscopic observation, the MIC determination based on the measurement of the turbidity does not have to be performed. Accordingly, it is possible to promptly confirm that growth inhibition cannot be achieved (it is possible to promptly determine omission from the target of the measurement of the turbidity). Thus, the MIC determination can be efficiently performed.

During the incubation, the culture plate 18 is disposed in the vicinity of the temperature controller 16, and the temperature of the culture liquid inside each of the wells in the culture plate 18 is controlled to be approximately 35° C. When the microscopic observation is performed or when the measurement of the turbidity is performed, the gripper 17 can move the culture plate 18 from the temperature controller 16 to the microscopic observation optical system and the turbidity measurement optical system 13 such that observation and measurement can be performed.

In addition, instead of a general microplate, a device (not illustrated) may be used as the culture plate 18 such that the culture liquid is sealed in a flow channel. For example, the bacterial identification test or the antimicrobial susceptibility test can be carried out by introducing the culture liquid and the bacterial suspension into a resin-made device having a culture liquid retention unit which corresponds to the well of the microplate. Similarly, in the embodiment of the present invention, microscopic observation can be carried out by introducing the culture liquid and the bacterial suspension containing the antibacterial agent into the device and covering both sides with transparent resins or glass. Accordingly, the device in which the culture liquid is sealed in the flow channel can be used in the test apparatus of the embodiment of the present invention.

The above-described database may be provided inside the computer 20 or may be provided in a storage device outside the test apparatus 10. In addition, the database does not have to be present in the physically same place as the test apparatus 10. The database may be configured to be connected to the test apparatus 10 via a network.

<Configuration Example of Optical System>

(1) Configuration Example of Optical System

FIG. 2 is a schematic diagram illustrating a configuration example of the microscopic observation optical system and the turbidity measurement optical system used in the bacteriological test apparatus 10. In FIG. 2, the culture plate 18 is irradiated with light from a light source 22. The light source 22 may be a white light source or a light source such as an LED having a spectrum in a certain wavelength range. The light source 22 is adjusted by a filter 23 so as to be in a suitable wavelength range. When the microscopic observation is performed, there is no need to particularly limit the wavelength. However, when the measurement of the turbidity is performed, unnecessary wavelength ranges are cut by the filter 23 such that the culture plate 18 is irradiated with light having the wavelength in the vicinity of 600 nm.

In a case of the microscopic observation, the culture plate 18 is irradiated with light from the light source 22 via a dichroic mirror 24 and an objective lens 25. The scattered light from the culture plate 18 passes through the objective lens 25 and is measured by a CCD element 27, and a microscopic observation image is acquired.

In a case of the measurement of the turbidity, the light from the light source 22 passes through the objective lens 25, and the culture plate 18 is irradiated with light for the measurement of the turbidity through the dichroic mirror 24. A portion of the irradiation light is transmitted through the culture plate 18, and the transmitted light is measured by a photodiode 26 installed above the plate 18. Meanwhile, the light which has passed through the dichroic mirror 24 is measured by a photodiode 26' installed on a side opposite to the light source 22. In accordance with the rule, the turbidity can be calculated based on the amount of light measured by the two photodiodes 26 and 26'.

(2) Another Configuration Example of Optical System

FIG. 3 is a schematic diagram illustrating another configuration example of the microscopic observation optical system and the turbidity measurement optical system which can be obtained in the bacteriological test apparatus 10. FIG. 2 illustrates an example in which the light source 22 is positioned below the culture plate 18. However, FIG. 3 illustrates an example in which a light source 32 is positioned above the culture plate 18.

In a case of the microscopic observation, the culture plate 18 is irradiated with light from the light source 32 via a filter 33 and a dichroic mirror 34. The light transmitted through the culture plate 18 passes through an objective lens 35 and measured by a CCD element 37, and a microscopic image is acquired.

In a case of the measurement of the turbidity, light from the light source 32 passes through the filter 33 and a portion thereof is reflected by the dichroic mirror 34. Then, the culture plate 18 is irradiated with the reflected light. A portion of the light transmitted through the culture plate 18 is reflected by a dichroic mirror 34' and a mirror 38 and is measured by a photodiode 36' installed below the culture plate 18.

In FIG. 3, the dichroic mirror 34' and the mirror 38 are disposed below the culture plate 18, and measurement is performed by the photodiode 36'. However, measurement may be performed by moving the positions of the objective lens 35 and the CCD element 37, and the position of the photodiode 36' through an XYZ stage.

Between the light which passes through the dichroic mirror 34 and the light which is further reflected by the dichroic mirror 34', the latter light has lower intensity. Therefore, before the measurement of the turbidity starts (before bacteria are introduced into the plate 18), it is necessary to input water to the culture plate 18, to measure light from the light source 32 by the photodiodes 36 and 36', and to correct the two measurement values thereof (turbidity) in advance such that the measurement values coincide with each other.

(3) Further another Configuration Example of Optical System

As illustrated in FIG. 4, the microscopic observation and the measurement of the turbidity may be respectively performed with respect to the wells different from each other in the culture plate 18. FIG. 4 illustrates a configuration example in which a plurality of light sources 42 and 42' are installed above the culture plate 18. The microscopic observation is performed with the light source 42 on one side, and the measurement of the turbidity is performed with the light source 42' on the other side.

The culture plate 18 is irradiated with light from the light source 42' on one side. The transmitted light passes through an objective lens 45 and is measured by a CCD element 47, and a microscopic image is acquired. The culture plate 18 is irradiated with light from the light source 42' on the other side, and the transmitted light is measured by a photodiode 46 installed below the culture plate 18.

In a case where the optical system illustrated in FIG. 4 is used, while the microscopic observation is performed with respect to each well in the microplate (culture plate 18), the measurement of the turbidity can be performed with respect to other wells. Accordingly, it is possible to reduce the number of times of scanning performed by the optical system in order to measure the wells in the microplate. In addition, in a case of performing scanning with the optical system for microscopic observation and the optical system for measurement of the turbidity, the two optical systems are retained in one mechanism so that the apparatus can be simplified. On the contrary, in a case where measurement is performed by moving the position of the microplate, a plurality of the wells can be simultaneously measured by disposing the optical system for microscopic observation and the optical system for measurement of the turbidity such that the positions thereof coincide with the gap between the wells in the microplate.

<Configuration of Test Apparatus in another Form>

FIG. 5 is a schematic diagram illustrating a schematic configuration of a bacteriological test apparatus 10', according to the embodiment of the present invention. Specifically, the bacteriological test apparatus 10' includes the cover 11, the placement table 12, a microscopic observation optical system 14, a turbidity measurement optical system 15, the temperature controller 16, the gripper 17 for transporting the culture plate 18, and the drive control device 19 which controls movement and positioning of the gripper 17. Moreover, the bacteriological test apparatus 10' includes the computer 20 for inputting information related to processing conditions and biological samples, information related to types and concentrations of antibiotics and the like, information related to patient specimens, and other various types of information.

When a test is performed by using the test apparatus 10' in FIG. 5, a bacterial suspension is introduced into the culture plate 18 and is mixed with a culture liquid included in each of the wells. Then, the temperature controller 16 is set to indicate a suitable temperature such that bacteria in the culture liquid included in each of the wells in the culture plate 18 are in a growth state. While performing culture, the gripper 17 moves the culture plate 18 to the microscopic observation optical system 14, and it is detected whether or not the bacteria growth by observing the bacteria included in each of the wells through the microscopic observation optical system 14. In addition, the gripper 17 moves the culture plate 18 to the turbidity measurement optical system 15 so that the turbidity of the culture liquid in each of the wells is measured. The microscopic observation and the measurement of the turbidity are performed for a suitable time input to the PC 20, and the drive control device 19 causes the gripper 17 to move the culture plate 18 to a suitable position. The data obtained as a result of the microscopic observation and the data obtained as a result of the measurement of the turbidity are stored and preserved in the control PC, thereby being utilized for the bacterial identification and the MIC determination.

<Configuration of Optical System>

FIGS. 6 and 7 are schematic diagrams respectively illustrating configuration examples of the microscopic observation optical system and the turbidity measurement optical system used in the bacteriological test apparatus 10', according to another embodiment of the present invention.

In FIG. 6, the culture plate 18 is irradiated with light from a light source 62. The light from the light source is adjusted to light having suitable intensity and a wavelength by a filter 63 and is reflected by a dichroic mirror (or a simple mirror) 64. The culture plate 18 is irradiated with the reflected light. Then, the light transmitted through the culture plate 18 passes through an objective lens 65 installed below the culture plate 18 and is measured by a CCD element 67, and an image is acquired.

In FIG. 7, the culture plate 18 is irradiated with light from a light source 72. The light from the light source 72 is adjusted to light having suitable intensity and a wavelength by a filter 73. The culture plate 18 is irradiated with the light for measurement of the turbidity reflected by a dichroic mirror 74, and the reflected light passes through an objective lens 75 installed below the culture plate 18 and is measured by a photodiode 76'. Meanwhile, the light which has passed through the dichroic mirror 74 is measured by a photodiode 76 installed on a side opposite to the light source 72. The turbidity is calculated based on the amount of light measured by the two photodiodes 76 and 76'.

<MIC Determination Processing>

FIG. 8 is a flow chart for describing the MIC determination processing executed by the bacteriological test apparatus 10 or the bacteriological test apparatus 10', according to the embodiment of the present invention. Actually, Steps 801 to 804 are work performed by an operator, and Steps S805 to S813 are executed by the computer (processor) 20 of the bacteriological test apparatus 10.

(i) Steps 801 to 803: An operator prepares a bacterial suspension which is the specimen to be introduced into the test apparatus 10 (S801), and the specimen is introduced into a culture plate (S802). Thereafter, the specimen is introduced into the bacteriological test apparatus (S803).

(ii) Step 804: The operator instructs the test apparatus 10 to start the test by inputting necessary information such as information for the specimen, and information for the antibacterial agents. Then, the culture plate 18 introduced into the apparatus is incubated by the test apparatus 10 to a temperature of approximately 35° C., and culture is performed.

Figure 15B:
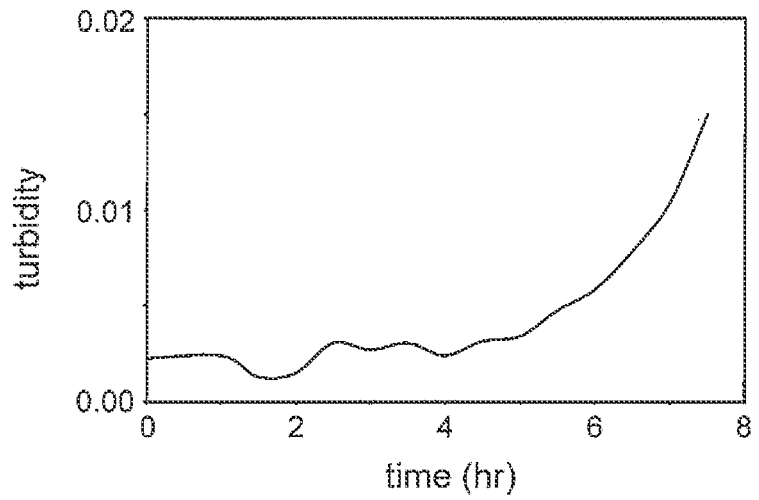

(iii) Step 805: The computer 20 acquires an image through microscopic observation of the wells in the culture plate at a time set in advance (for example, every predetermined time or the like) by using the microscopic optical system (FIG. 1) included in the optical system 13 or the microscopic optical system 14 (FIGS. 15A and 15B).

(iv) Steps 806 and 807: The computer 20 carries out processing necessary for the image acquired in Step 805 (S806), thereby attempting the MIC determination based on the image data acquired through a microscope (S807).

(v) Steps 808 and 809: The computer 20 performs the measurement of the turbidity of each well in the culture plate 18 by using the turbidity measurement optical system or the turbidity measurement optical system 15 included in the optical system 13 (S808), and the computer 20 determines whether or not the turbidity data exceeds a predetermined threshold value, thereby attempting the MIC determination (S809).

(vi) Step 810: The computer 20 performs matching processing by comparing the image information or the turbidity information in the database (refer to FIG. 9) with the acquired image information or the measured turbidity information, thereby attempting the MIC determination.

(vii) Step 811: The computer 20 determines whether the bacterial growth has proceeded so as to be ready for the MIC determination, that is, whether the incubation is to continue. In a case where the growth of the bacteria has not proceeded and the state is not ready for the MIC determination (in a case of Yes in S811), the processing shifts to Step 812. In a case where there is no need to continue the incubation (in a case of No in S811), the processing shifts to Step 813.

(viii) Step 812: The computer 20 determines whether a predetermined time (for example, six hours) has elapsed after the start of the test. In a case where a predetermined time has elapsed (in a case of Yes in S812), the processing shifts to Step 808, and the measurement of the turbidity is performed again. In a case where a predetermined time has not elapsed (in a case of No in S812), the processing shifts to Step 805, and the incubation continues by repeating the processing from the step of acquiring an image.

(ix) Step 813: In a case where the MIC determination for the antibacterial agents included in the culture plate is completed, or in a case where processing of the antibacterial agents ready for the MIC determination is completed and it is determined to be difficult to determine the remaining antibacterial agents (growth inhibition cannot be achieved), the computer 20 determines the final MIC by comparing the MIC determined based on the image (excluding the determination result in which growth inhibition cannot be achieved), the MIC determined based on the turbidity, and the data accumulated in the database, thereby ending the test. In addition, in a case where it is determined, based on the image, that growth inhibition cannot be achieved, comparison with respect to the database is not performed, thereby ending the test.

(x) Others: The MIC determination processing is automatically executed based on the conditions set to each culture plate. A plurality of the culture plates can be simultaneously installed in the bacteriological test apparatus 10 or 10'. However, the conditions of each culture plate may vary, or the processing may be carried out under the same conditions. In addition, conditions such as performing the MIC determination based on only the image, and performing the MIC determination based on only the turbidity may be set, or conditions such as carrying out the processing while inevitably performing comparison with respect to the database may be set.

<Image Comparison>

Figures 17A, 17B, 17C:
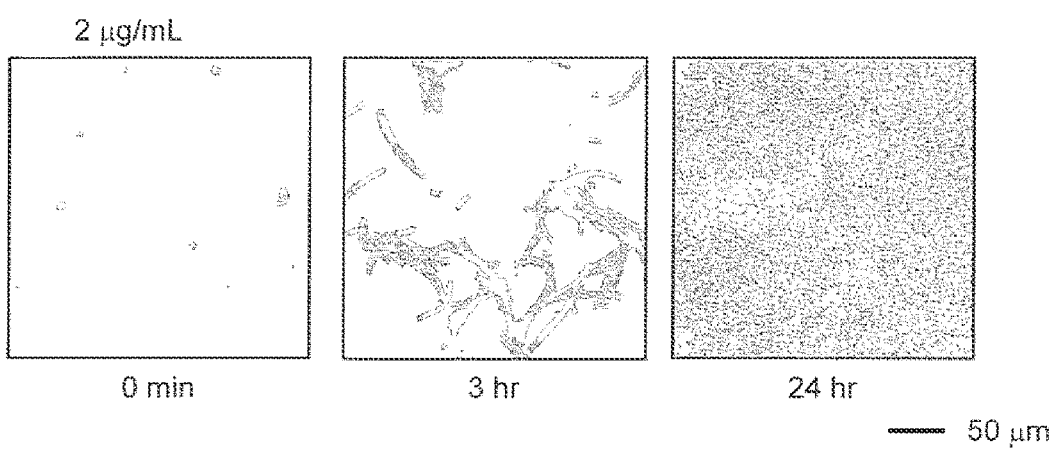
FIGS. 17A-17C are images of Example 2 obtained through the susceptibility test (Exemplary Embodiment 2) performed by the bacteriological test apparatus.

FIG. 9 is a diagram illustrating a concept of comparison between an acquired image and the image in the database. In the antimicrobial susceptibility test, culture is performed under the conditions in which the antibacterial agents varied in type and concentration are applied to the bacteria which are the test target, and the MIC is determined by examining whether or not the bacteria can grow. The database stores the images of the bacteria in a case where culture is performed with particular types and concentrations of the antibacterial agent for each species of the bacteria. Even though the species of the bacteria are the same as each other, when the strains thereof are different from each other, susceptibility with respect to an antimicrobial varies. Therefore, the MIC is determined by performing comparison of the image which is similar to an image of the test target acquired from a plurality of images stored in the database under the conditions of types and concentrations of the antibacterial agent. In addition, regarding a certain antibacterial agent, since the image in the database and the image of the test target are compared in various concentrations, the MIC can be accurately performed. For example, as illustrated in FIG. 17B, in a case where the bacteria are in an elongated state, it is confirmed that there is the effect of the antibacterial agent. However, eventually, it is confirmed that extinction of the bacteria has failed (refer to FIG. 17C). Therefore, it is assumed that the MIC becomes higher than the concentration thereof.

In addition, instead of performing comparison of the images, identification or antimicrobial susceptibility of the bacteria may be determined by performing comparison of the bacterial numbers present in the image; the areas of the bacteria present in the image (confirmed based on the number of pixels in the image); and feature values such as the circularity, the aspect ratio, and the perimeter length of the bacterium extracted from the image. The feature values such as the average area, the circularity, the aspect ratio, and the perimeter length of the bacterium are extracted from the image stored in the database in advance, and the feature values are extracted from an image acquired through the test, thereby performing the MIC determination by comparing the feature values with each other. In a case where an enormous amount of the data is included in the control PC, a form of performing comparison may be adopted by storing an image database or various feature values of the bacteria in the server and having access thereto when the MIC determination is performed. Since the MIC can be determined by utilizing the information obtained through the microscopic observation, the MIC can be determined not only from the result of the measurement of the turbidity, but also from the image. Thus, determination can be more accurately performed.

Exemplary Embodiment 1

FIGS. 10A to 13D are diagrams illustrating the results obtained by applying the present invention. FIGS. 10A to 13D illustrate images obtained by performing a susceptibility test with respect to levofloxacin of *Enterococcus faecalis* (ATCC29212) by using the bacteriological test apparatus 10 of the embodiment of the present invention. FIGS. 10A-10D illustrate images of the states of the bacteria in a Mueller-Hinton culture medium not containing levofloxacin, respectively captured after (a) zero minutes, (b) 90 minutes, (c) 150 minutes, and (d) 210 minutes from the start of culture. Similarly, FIGS. 11A-11D illustrate images of *Enterococcus faecalis* in the culture liquid containing levofloxacin of 0.5 μg/mL. FIGS. 12A-12D illustrate images thereof in the culture liquid containing 1.0 μg/mL. FIGS. 13A-13D illustrate images thereof in the culture liquid containing levofloxacin of 2.0 μg/mL. The target objects which appear to be white in FIGS. 10A to 13D are the *Enterococcus faecalis*.

In FIGS. 10A-10D and 11A-11D, a state where *Enterococcus faecalis* grew and was divided in a chain state with the lapse of time after the start of culture could be observed. Meanwhile, in FIGS. 12A-12D and 13A-13D, the *Enterococcus faecalis* was divided to a certain extent till the times of FIGS. 12C and 13C (after 150 minutes). However, a state of being seldom divided could be observed thereafter.

FIG. 14 is a graph plotted with a state where the *Enterococcus faecalis* grows. FIG. 14 is a graph obtained by calculating the areas of the *Enterococcus faecalis* based on the images of FIGS. 10A to 13D and plotting the areas of the *Enterococcus faecalis* periodically after the start of culture. In cases of the graphs (i) and (ii) respectively having the concentrations of levofloxacin of 0 μg/mL and 0.5 μg/mL, it was confirmed that the areas of the *Enterococcus faecalis* in the images increased with the lapse of time. Meanwhile, in cases of the graphs (iii) and (iv) respectively having the concentrations of levofloxacin of 1 μg/mL and 2 μg/mL, the *Enterococcus faecalis* slightly increased till after approximately 150 minutes. However, the *Enterococcus faecalis* did not increase thereafter. According to the graphs, it was confirmed that the minimum inhibitory concentration (MIC) with respect to the levofloxacin in the strain of the used *Enterococcus faecalis* was 1 μg/mL.

FIGS. 15A and 15B are graphs illustrating the result of FIGS. 10A-10D, which is obtained by measuring the turbidity of the culture liquid in the wells to which *Enterococcus faecalis* containing no levofloxacin is input, by using the bacteriological test apparatus 10 of the present invention. FIG. 15A is a graph illustrating the change of the turbidity till after approximately seven hours from the start of culture, and FIG. 15B is an enlarged view of FIG. 15A. According to the graphs of FIGS. 15A and 15B, it was confirmed that the turbidity began to increase after approximately six hours from the start of culture. In the bacteriological test apparatus in the related art, it has been determined that bacteria are reproduced when the turbidity becomes equal to or greater than approximately 0.1 (threshold value). Therefore, it is possible to know that MIC determination cannot be made by the time of seven hours. In the method in the related art, culture needs to be performed for at least approximately 12 hours. However, in the present invention, it could be confirmed that the MIC determination could be made with the culture performed for approximately three hours.

Exemplary Embodiment 2

Figures 16A, 16B, 16C:
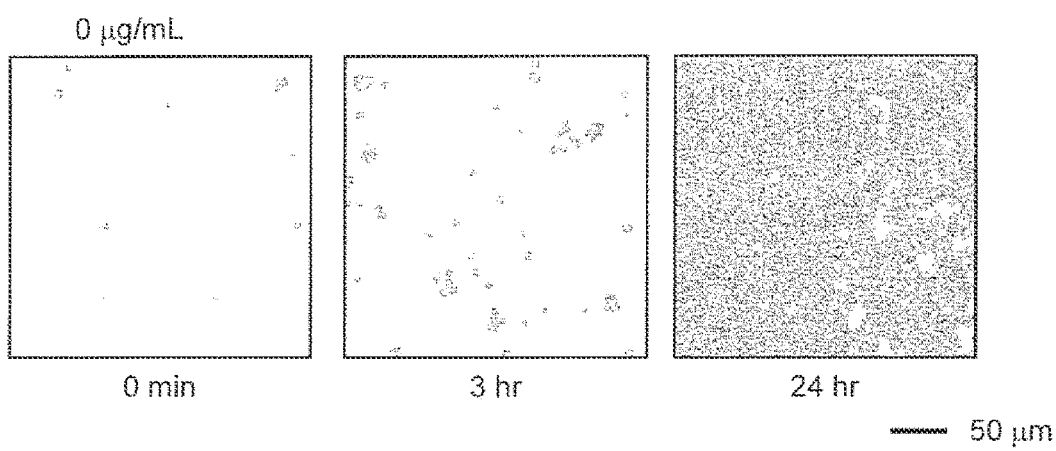
FIGS. 16A-16C are images of Example 1 obtained through a susceptibility test (Exemplary Embodiment 2) performed by the bacteriological test apparatus.

FIGS. 16A to 18C are diagrams illustrating results of a susceptibility test with respect to ampicillin of *E. coli* (ATCC25922) performed by using the bacteriological test apparatus of the present invention. FIGS. 16A to 18C are images obtained by culturing the *E. coli* in Mueller-Hinton culture mediums respectively containing ampicillin having the concentrations of 0 μg/mL, 2 μg/mL, and 16 μg/mL, performing image processing of a line extracting filter and the like onto microscopic images respectively captured after (a) 0 hours, (b) 3 hours, and (c) 24 hours from the start of culture, and performing binarization. The target objects appearing black in FIGS. 16A to 18C are the *E. coli*. In FIGS. 16A-16C, it could be confirmed that the *E. coli* which was small in number immediately after the start of culture (FIG. 16A) grew after three hours (FIG. 16B), and was spreading in almost the entire region of the image after 24 hours (FIG. 16C).

In FIGS. 17A-17C, it could be confirmed that bacteria having normal shapes immediately after the start of culture (FIG. 17A) were in elongated states after three hours (FIG. 17B) due to effect of ampicillin. In addition, it could be confirmed that the *E. coli* was being spreading in almost the entire region of the image after 24 hours (FIG. 17C). FIG. 17B illustrates that change in the shape of the *E. coli* caused by inhibitory effect of cell wall synthesis of the ampicillin can be observed through the bacteriological test apparatus of the present invention. Since the partition wall synthesis in the cell wall synthesis was inhibited, the *E. coli* could not be divided and was elongated. However, as seen in FIG. 17C, it could be confirmed that the *E. coli* was below the level of sterilization in the concentration of 2 µg/mL and grew after 24 hours.

Figures 18A, 18B, 18C:
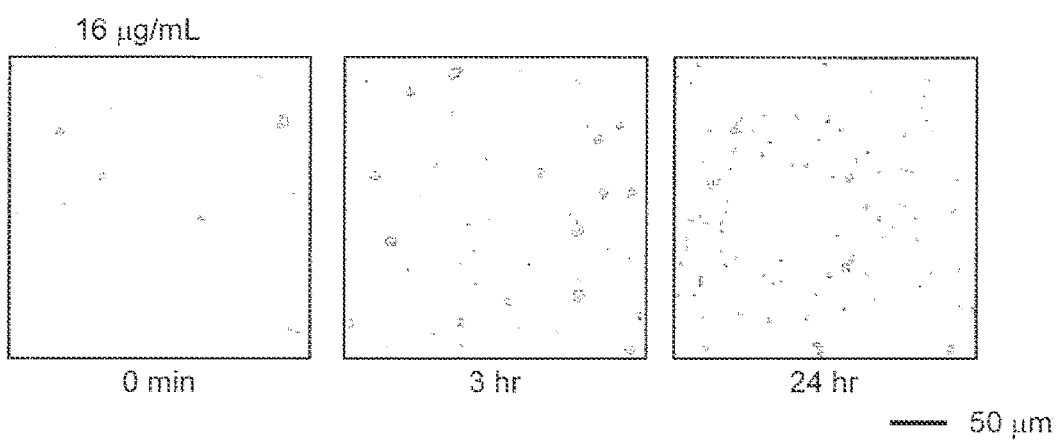
FIGS. 18A-18C are images of Example 3 obtained through the susceptibility test (Exemplary Embodiment 2) performed by the bacteriological test apparatus.

In FIGS. 18A-18C, since the concentration of ampicillin was 16 µg/mL which was high, it could be confirmed that not only the synthesis of the partition walls in the cell wall synthesis but also the synthesis of the side wall was inhibited, and the bacteria did not grow without being elongated.

FIG. 19 is a graph obtained by calculating the areas of the *E. coli* in the images of FIGS. 16A to 18C and plotting the areas thereof periodically. In cases where the concentrations of the ampicillin are respectively 0 µg/mL and 2 µg/mL as illustrated in the graphs (i) and (ii), it was able to be checked that the areas of the *E. coli* in the images increased with the lapse of time. Meanwhile, when the concentration of the ampicillin was 16 µg/mL as illustrated in the graph (iii), the *E. coli* could not be divided due to effect of the ampicillin, and the areas seldom increased. In this manner, it was possible to obtain the MIC with respect to the ampicillin of the used *E. coli* based on the graph achieved by monitoring the change in the areas of the bacteria in the images. It could be confirmed that the antimicrobial susceptibility test which requires overnight culture in the related art could be carried out in a short time by using the bacteriological test apparatus of the present invention.

Exemplary Embodiment 3

Figure 21A:
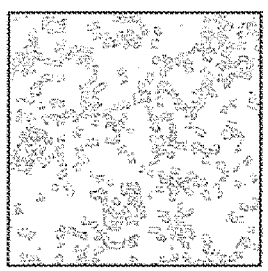
FIGS. 21A-21D are images of Example 2 obtained through the susceptibility test (Exemplary Embodiment 3) performed by the bacteriological test apparatus.
Figure 21B:
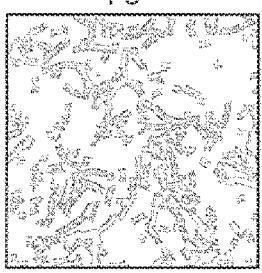
Figure 21C:
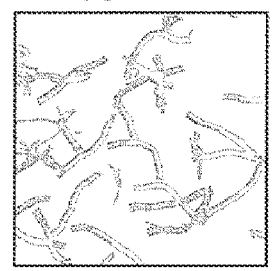
Figure 21D:
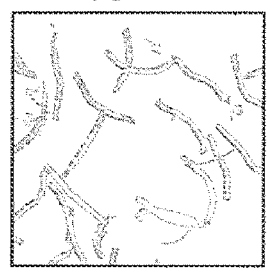

FIGS. 20A-20D and 21A-21D are diagrams illustrating results of a susceptibility test of *E coli* (ATCC35218) treated with cefazolin performed by using the bacteriological test apparatus of the present invention. FIGS. 20A to 20D are microscopic images which are obtained by culturing the *E. coli* in Mueller-Hinton culture mediums respectively containing cefazolin having concentrations of 0 µg/mL, 0.5 µg/mL, 1 µg/mL, and 2 µg/mL, and captured after three hours from the start of culture. The target objects vaguely appearing in the images are the bacteria. FIGS. 21A to 21D are images obtained by respectively performing image processing onto the images of FIGS. 20A to 21D, performing edge detection, and performing binarization thereafter. The target objects appearing black in FIGS. 21A-21D are the *E. coli*. In FIGS. 21A-21D, it could be confirmed that the *E coli* grew after three hours in the culture medium containing no cefazolin (FIG. 21A) and in the culture medium containing the cefazolin having the concentration of 0.5 µg/mL (FIG. 21B). Meanwhile, in FIGS. 21C and 21D, it could be confirmed that the *E. coli* did not quite grow after three hours and was elongated.

Figure 22A:
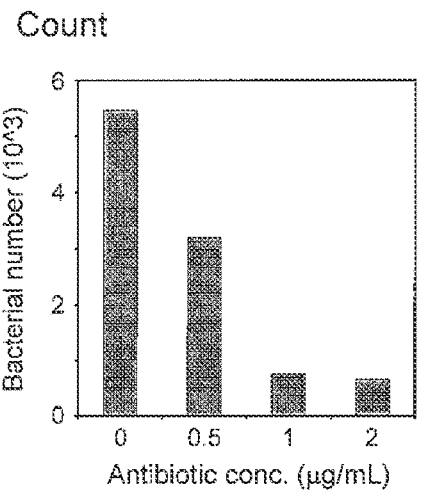
FIGS. 22A-22F are graphs of feature values of bacteria extracted from a microscopic observation image of the bacteria obtained through the susceptibility test (Exemplary Embodiment 3) performed by the bacteriological test apparatus.
Figure 22B:
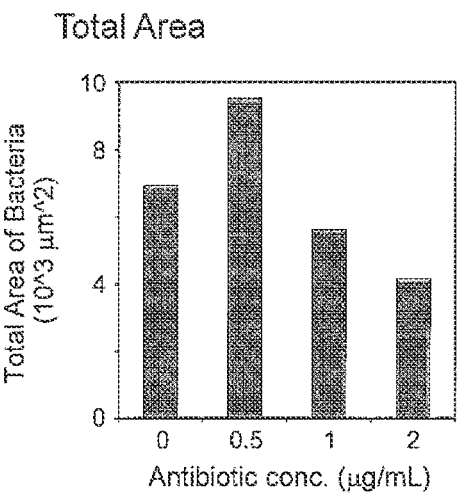
Figure 22C:
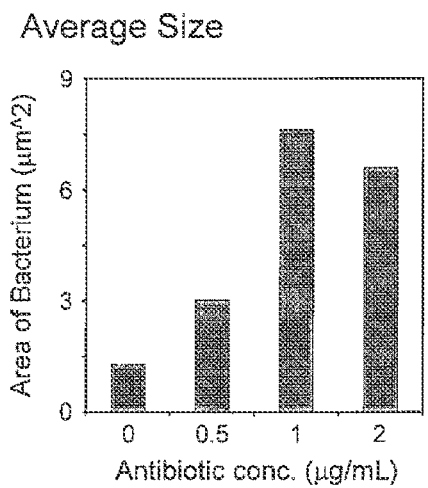
Figure 22D:
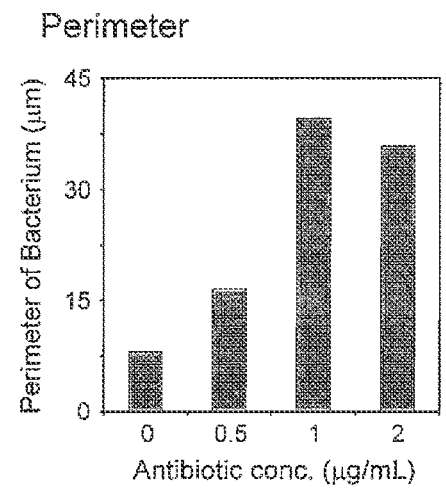
Figure 22E:
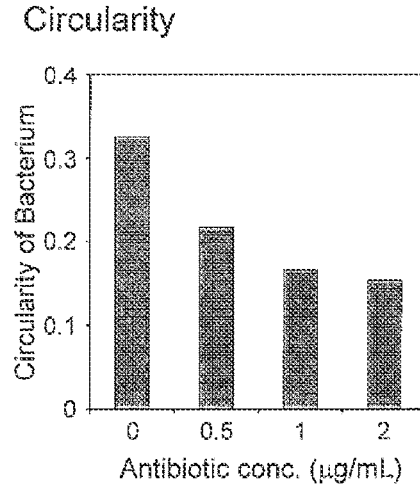
Figure 22F:
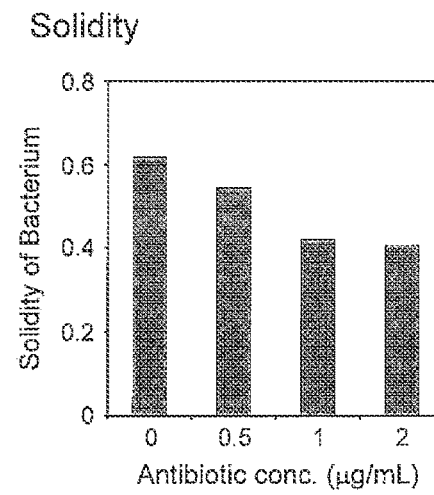

FIGS. 22A-22F are graphs obtained by extracting the feature values of the bacteria from the image of FIGS. 20A-20D. FIG. 22A is a graph illustrating the bacterial number in a microscopic image. It could be confirmed that the bacterial number increased through growth in a state of having no antibacterial agent or containing cefazolin having the concentration of 0.5 µg/mL. In contrast, the bacteria did not quite grow in a state of containing cefazolin having the concentrations of 1 µg/mL and 2 µg/mL. FIG. 22B is a graph illustrating the areas of the bacteria in the microscopic image. FIG. 22C is a graph illustrating the average values of the areas per one bacterium obtained based on FIGS. 22A and 22B. Regarding the average value of the areas per one bacterium, it could be confirmed that the area increased in a state of containing cefazolin having the concentration of 0.5 µg/mL compared to the area having no antibacterial agent, and the area per one bacterium further increased in a state of having the concentrations of 1 µg/mL and 2 µg/mL. As it also could be confirmed in FIGS. 21A-21D, the facts thereof indicate that the bacteria are elongated due to effect of cefazolin. FIGS. 22D to 22F are graphs respectively showing the perimeter length, the circularity, and the solidity (an index showing how the shape is close to a circle) per one bacterium. As the results of the elongated bacteria, it could be confirmed that the perimeter length increased in FIG. 22D, the circularity defined through $4\pi \times$ the area/(the perimeter length)$^2$ was lowered in FIG. 22E, and the solidity defined through the area/the projection area is lowered in FIG. 22F.

Therefore, in a case where the bacteria were elongated due to effect of the antibacterial agent even though the bacterial number did not increase, a phenomenon in which the areas of the bacteria increase could be confirmed. The above-referenced information is information which cannot be obtained through the measurement of the turbidity in the related art. The MIC determination can be more accurately performed by adding the above-referenced information and utilizing in the MIC determination.

CONCLUSION

The test apparatus according to the embodiment of the present invention includes (i) a microscopic observation optical system that has a light source for performing microscopic observation of each of the wells in the culture plate for bacterial identification culture or the antimicrobial susceptibility test, a mirror, an objective lens, and a CCD for acquiring an image; (ii) a turbidity measurement optical system that has a light source for performing measurement of absorbance of each of the wells in the culture plate, a mirror, and a photodiode; (iii) an XYZ stage that changes the position of the culture plate in order to observe or measure each of the wells; and (iv) a temperature control function. Here, the light source and the mirror for performing microscopic observation may be the same as the light source and the mirror for performing measurement of absorbance or may be separately installed. The turbidity (absorbance in the vicinity of the wavelength of 600 nm) can be measured by installing a suitable bandpass filter between the light source and the mirror. The microscopic observation in white light can be performed by switching the bandpass filter with a different filter. In addition, a mirror may be installed in front of the CCD acquiring the microscopic observation image, or the photodiode for measuring absorbance, and the mirror may be switched when performing measurement thereof.

The culture plate is installed on the XYZ stage, culture is performed while the temperature is controlled to be approximately 35° C., the XYZ stage is operated at the set time, and the state of each of the wells in the culture plate is observed. Regarding controlling of the XYZ stage, switching of the bandpass filter, switching of the mirror, setting of the temperature controller, and the like, controlling is performed by setting the conditions using the control PC set in the test apparatus. In addition, the control PC also sets the time to perform observation of the wells in the culture plate or the time to perform measurement of absorbance and records the result thereof.

The microscopic observation of the shape and the number of bacteria in the wells is performed or the measurement of the turbidity of the culture liquid in the wells is performed while the test apparatus performs culture. It is determined whether or not the bacteria grow in which wells, based on the result of the microscopic observation. The species or the genus of the bacteria is identified based on the combinations of wells in which the bacteria grow, and the antimicrobial susceptibility is determined. It is also determined whether or not the bacteria grow in which wells, based on the result of the measurement of the turbidity. The species or the genus of the bacteria is identified based on the combinations of wells in which the bacteria grow, and the antimicrobial susceptibility is determined. The identification of bacteria or determination of antimicrobial susceptibility can be performed by comparing the feature values extracted from the image information of the database (the database storing information such as the combinations of the wells in which the bacteria grow and the antimicrobials by which growth of the bacteria is inhibited) stored in the control PC, or the image information such as the number bacteria present in the image, the areas of the bacteria present in the image, the circularity of the bacteria, the aspect ratio, and the perimeter length. In a case where an enormous amount of data is included in the database, a form in which the data is stored in a server and comparison is performed through access thereto at the time of the MIC determination may be adopted.

It is possible to perform the microscopic observation of bacteria in each of the wells in the culture plate and to perform the measurement of the turbidity of the culture liquid in each of the wells by using the test apparatus of the embodiment of the present invention. The bacteriological test apparatus in the related art monitors the growth of bacteria by measuring the turbidity of the culture liquid. However, it takes approximately five to six hours from the start of culture for the turbidity of the culture liquid to start increasing in accordance with the growth of the bacteria. In the antimicrobial susceptibility test, the culture liquid and the quantity of bacteria to be used are fixed, and it is not easy to reduce the time of test by performing the measurement of absorbance. Generally, it is because the time until the bacteria are divided and reach the concentration in which the turbidity of the culture liquid increases is determined due to the division speed of the bacteria, and the speed thereof does not drastically change under normal culture conditions.

However, the division state of the bacteria can be monitored by performing the microscopic observation using an objective lens of approximately twenty magnifications so that it is possible to determine whether or not each of the bacteria is divided. Accordingly, when the phase shifts from an induction phase (lag phase) to a logarithmic phase (log phase), it is possible to determine whether or not the bacteria are divided. Generally, the growth profile of bacteria shifts from the induction phase to the logarithmic phase within 30 minutes to 3 hours. Therefore, it is possible to determine whether the bacteria grow faster than the determination performed based on the turbidity.

In addition, the change in the shape of bacteria can be recognized as an image through the microscopic observation. Therefore, in the antimicrobial susceptibility test, it is possible to obtain the information related to the shape of bacteria such as elongated bacteria or spherical bacteria caused by the effect of the antibacterial agent. Generally, β-lactam antibacterial agents are known to be elongated when acting on *bacillus*. It is possible to perform highly accurate determination of antimicrobial susceptibility by utilizing such change in the shape of bacteria. Information regarding the types of the antibacterial agents, the types of the bacteria to which the antibacterial agents are applied, and the combinations where the shape of bacteria changes is stored in the database in advance, and compared with the images obtained through the test. Thus, it is possible to improve the reliability of the determination of the antimicrobial susceptibility.

In an antimicrobial susceptibility test of bacteria, culture liquids respectively containing various types of antibacterial agents having various concentrations are input to the wells in the culture plate, and the bacteria which are the test target are cultured therein. It is possible to promptly determine whether or not the bacteria grow in which well. Accordingly, the antimicrobial susceptibility test can be promptly performed. Similarly, in a bacterial identification test, various types of culture liquids are respectively input to the wells in the culture plate, and the bacteria which are the test target are cultured therein. The bacteria are identified based on whether the bacteria growth in which well. However, the presence or absence of the bacterial growth can be promptly determined. Therefore, the bacterial identification test also can be promptly performed.

The present invention also can be realized by a program code of software which realizes the function of the embodiment. In this case, a storage device in which the program code is recorded is provided in a system or an apparatus, and a computer (otherwise, a CPU or an MPU) of the system or the apparatus reads out the program code stored in the storage device. In this case, the program code itself which is read out from the storage device realizes the above-described function of the embodiment, and the program code itself and the storage device storing the program code are configured to be the present invention. As the storage device for supplying such a program code, for example, a flexible disk, a CD-ROM, a DVD-ROM, a hard disk, an optical disk, a magneto-optic disk, a CD-R, a magnetic tape, a non-volatile memory card, and a ROM are used.

In addition, based on the instruction of the program code, an operating system (OS) driven in the computer, or the like may perform a portion or the entirety of the actual processing, and the above-described function of the embodiment may be realized through the processing. Moreover, the program code read out from the storage device may be written in a memory in the computer. Thereafter, based on the instruction of the program code thereof, the CPU or the like of the computer may perform a portion or the entirety of the actual processing, and above-described function of the embodiment may be realized through the processing.

Moreover, the program code of the software which realizes the function of the embodiment may be delivered via a network. Accordingly, the program code may be stored in storage means such as the hard disk or the memory of the system or the apparatus; or the storage device such as a CD-RW and a CD-R. Thus, when in use, the computer (otherwise, the CPU or the MPU) of the system or the apparatus may read out and execute the program code stored in the storage means or the storage device.

Last, the process and the technique described herein are not essentially related to any particular apparatus, and it is necessary to understand that the process and the technique can be implemented by any suitable combination of the components. Moreover, various types of general-purpose devices can be used in accordance with the instructed description herein. In order to execute the above-described steps of the method, it may be profitable to establish a dedicated apparatus. In addition, various types of invention can be formed by appropriately combining multiple configuration elements disclosed in the embodiment. For example, some configuration elements may be deleted from the overall configuration elements indicated in the embodiment. Moreover, the configuration elements in the embodiments different from each other may be appropriately combined together. In the present invention, description has been given regarding the specified examples for the explanation in all viewpoints, not for the limitation. Those skilled in the art can know that there are many suitable combinations of hardware, software, and firmware to carry out the present invention. For example, the above-referenced software may be implemented by a wide-range program or a script language such as an assembler, C/C++, perl, Shell, PHP, and Java (registered trademark).

Moreover, in the above-described embodiment, the control lines or the information lines considered to be necessary in the description are indicated. All the control lines or the information lines in a product are not necessarily indicated. All the configurations may be connected to each other.

REFERENCE SIGNS LIST 10, 10' . . . TEST APPARATUS; 11 . . . COVER; 12 . . . PLACEMENT TABLE; 13 . . . OPTICAL SYSTEM (MICROSCOPIC OBSERVATION OPTICAL SYSTEM AND TURBIDITY MEASUREMENT OPTICAL SYSTEM); 14 . . . MICROSCOPIC OBSERVATION OPTICAL SYSTEM; 15 . . . TURBIDITY MEASUREMENT OPTICAL SYSTEM; 16 . . . TEMPERATURE CONTROLLER; 17 . . . GRIPPER; 18 . . . CULTURE PLATE; 19 . . . DRIVE CONTROL DEVICE; 20 . . . PC (COMPUTER); 22, 32, 42, 42', 62, 72 . . . LIGHT SOURCE; 23, 33, 63, 73 . . . FILTER; 24, 34, 34', 74 . . . DICHROIC MIRROR; 38, 64 . . . MIRROR; 25, 35, 45, 65, 75 . . . OBJECTIVE LENS; 26, 26', 36, 36', 46, 76, 76' . . . PHOTODIODE; 27, 37, 47, 67 . . . CCD ELEMENT

The invention claimed is:

1. A test apparatus configured to perform an identification test or an antimicrobial susceptibility test of bacteria or fungi, the test apparatus comprising:
a temperature control unit that controls a temperature of a culture plate having a plurality of wells and retaining a culture liquid that contains the bacteria or the fungi in each well;
a microscopic observation optical system configured to perform microscopic observation of the bacteria or the fungi in the culture liquid included in each well of the culture plate;
a turbidity measurement optical system configured to perform measurement of turbidity of the culture liquid that is retained in each well of the culture plate;
a transportation mechanism configured to transport the culture plate between the temperature control unit and the microscopic observation optical system; and
a processor configured to perform an identification test or an antimicrobial susceptibility test of the bacteria or the fungi in accordance with a program,
wherein:
the microscopic observation optical system includes a light source and an imaging device that captures light emitted from the light source and having passed through the culture plate,
the microscopic observation optical system is configured to acquire a microscopic observation image of the bacteria or the fungi in the culture liquid included in each of the wells in the culture plate, the microscopic observation image being a transmission image of each of the wells in the culture plate,
the turbidity measurement optical system measures turbidity of a bacterial suspension contained in the culture liquid that is retained in each well of the culture plate, and
the processor is configured to
perform an identification test or an antimicrobial susceptibility test of the bacteria or the fungi from the microscopic observation image of the bacteria or the fungi, thereby acquiring a result of a first identification test or a first antimicrobial susceptibility test,
perform determination of the antimicrobial susceptibility test of the bacteria or the fungi from the measurement of turbidity, thereby acquiring a result of a second identification test or a second antimicrobial susceptibility test, and
perform final determination of the identification test or the antimicrobial susceptibility test based on the results of the first and second identification tests or the first and second antimicrobial susceptibility tests, and data stored in a database in advance.

2. The test apparatus according to claim 1, wherein:
the temperature control unit cultures the bacteria or the fungi in the culture liquid that is retained in each well of the culture plate, and
the microscopic observation optical system allows microscopic observation of a bacterial suspension contained in the culture liquid that is retained in each well of the culture plate, and enables the identification test or the antimicrobial susceptibility test of the bacteria or the fungi.

3. The test apparatus according to claim 1, wherein the processor is configured to perform the final determination of the identification test or the antimicrobial susceptibility test by comparing the results of the first and second identification tests or the first and second antimicrobial susceptibility tests with the data stored in the database in advance.

4. The test apparatus according to claim 1, wherein:
the temperature control unit cultures the bacteria or the fungi in the culture liquid that is retained in each well of the culture plate,
the microscopic observation optical system allows microscopic observation of a bacterial suspension contained in the culture liquid that is retained in each well of the culture plate, and enables a first identification test or a first antimicrobial susceptibility test, and
the turbidity measurement optical system allows measurement of turbidity of the bacterial suspension contained in the culture liquid that is retained in each well of the culture plate, and enables a second identification test or a second antimicrobial susceptibility test.

5. The test apparatus according to claim 3, wherein the processor is configured to perform matching of a division state of the bacteria or the fungi by comparing an image obtained by performing observation through the microscopic optical system with an image stored in the database in advance and perform determination of the identification test or the antimicrobial susceptibility test of the bacteria or the fungi.

6. The test apparatus according to claim 5, wherein the processor is configured to compare feature values derived from each bacteria or fungi with feature values derived from each bacteria or fungi extracted from the image in the database, thereby performing determination of the identification test or the antimicrobial susceptibility test of the bacteria or the fungi.

7. The test apparatus according to claim 1, wherein
the turbidity measurement optical system has a configuration independent of the microscopic observation optical system,
the transportation mechanism transports the culture plate between the temperature control unit and the microscopic observation optical system and between the temperature control unit and the turbidity measurement optical system, and microscopic observation and measurement of turbidity are simultaneously performed with light emitted from one light source with respect to the wells different from each other in the culture plate.

\* \* \* \* \*